US007989591B2

(12) United States Patent
Sinclair et al.

(10) Patent No.: US 7,989,591 B2
(45) Date of Patent: Aug. 2, 2011

(54) PROTEIN LATTICE

(75) Inventors: John Charles Sinclair, Oxford (GB); Martin Edward Mäntylä Noble, Oxford (GB)

(73) Assignee: Isis Innovation Limited, Oxford (GB)

( * ) Notice: Subject to any disclaimer, the term of this patent is extended or adjusted under 35 U.S.C. 154(b) by 362 days.

(21) Appl. No.: 10/530,795

(22) PCT Filed: Oct. 8, 2003

(86) PCT No.: PCT/GB03/04306
§ 371 (c)(1),
(2), (4) Date: Nov. 7, 2005

(87) PCT Pub. No.: WO2004/033487
PCT Pub. Date: Apr. 22, 2004

(65) Prior Publication Data
US 2006/0173166 A1    Aug. 3, 2006

(30) Foreign Application Priority Data
Oct. 8, 2002  (GB) .................................. 0223323.7

(51) Int. Cl.
C07K 14/00 (2006.01)
C07K 1/00 (2006.01)
C07H 21/04 (2006.01)
C12N 15/63 (2006.01)
C12N 15/85 (2006.01)
C12N 15/86 (2006.01)
C12N 1/21 (2006.01)
C12N 1/15 (2006.01)
C12N 5/14 (2006.01)
C12N 1/19 (2006.01)

(52) U.S. Cl. ...... 530/350; 530/402; 536/23.1; 536/23.4; 435/320.1; 435/325; 435/252.3; 435/254.11; 435/419; 435/254.2

(58) Field of Classification Search .................. None
See application file for complete search history.

(56) References Cited

U.S. PATENT DOCUMENTS
2008/0097080 A1    4/2008  Sinclair et al.
2010/0202672 A1    8/2010  Sinclair et al.

FOREIGN PATENT DOCUMENTS
WO    WO 96/17055        6/1996
WO    WO 00 68248  A    11/2000
WO    WO 01/85962  A1   11/2001
WO    WO 2008/145951 A1 12/2008

OTHER PUBLICATIONS

Narayana et al., The Dimerization Domain of HNF-1alpha: Structure and Plasticity of an Intertwined Four-helix Bundle with Application to Diabetes Mellitus, J. Mol. Biol. (2001) 310, 635-658.*
Ngo et al., in The Protein Folding Problem and Tertiary Structure Prediction, 1994, Merz et al. (ed.), Birkhauser, Boston, MA, pp. 433 and 492-495.*
Hestenes, Retrieved from the Internet at <http://modelingnts.la.asu.edu/pdf/crystalsymmetry.pdf>, [Retrieved on Mar. 18, 2008].*
Merriam-Webster On-line Dictionary Definition of "monomer", Retrieved from the Internet at www.merriam-webster.com, [Retrieved on Mar. 18, 2008].*
Giege et al. Crystallogenesis of Biological Macromolecules: Facts and Perspectives. Acta Cryst., 1994, D50: 339-350.*
Branden et al. ("Introduction to Protein Structure Second Edition", Garland Publishing Inc., New York, 1999).*
Drenth ("Principles of X-ray Crystallography," Springer, New York, 1995).*
Kierzek et al., Biophys Chem 91:1-20, 2001.*
Dotan et al. (Self-Assembly of a Tetrahedral Lectin into Predesigned Diamondlike Protein Crystals, Angew. Chem. Int. Ed. 1999, 38, No. 16, pp. 2363-2366).*
Grant et al.(The crystal structure of Dps, a ferritin homolog that binds and protects DNA, Nature Structural Biology, vol. 5, No. 4, 1998, pp. 194-303).*
Merriam-Webster dictionary, retrieved from the Internet: <http://www.merriam-webster.com/dictionary/fused?show=1&t=1287510761>, retrieved on Oct. 19, 2010.*
Berman, H. M., et al., "The Protein Data Bank," *Nucleic Acids Research*, 28(1): 235-242 (2000).
Ghadiri, M.R., et al., "Self-assembling Organic Nanotubes Based on a Cyclic Peptide Architecture," *Nature*, 366: 324-327 (1993).
Nooren, I.M.A., et al., "Structural Characterisation and Functional Significance of Transient Protein-Protein Interactions," *J. Mol. Biol.*, 325(5): 991-1018 (2003).
Padilla, J. E., et al., "Nanohedra: Using symmetry to design self assembling protein cages, layers, crystals, and filaments," *PNAS*, 98(5) 2217-2221 (2001).
Pleschberger, M., et al., "Generation of a Functional Monomolecular Protein Lattice Consisting of an S-Layer Fusion Protein Comprising the Variable Domain of a Camel Heavy Chain Antibody," *Bioconjugate Chem.*, 14(2): 440-448 (2003).
Ringler, P. and Schulz, G.E., "Self-Assembly of Proteins into Designed Networks," Science, 302:106-109 (Oct. 3, 2003).
Notification of Transmittal of the International Search Report (ISR) and the Written Opinion (WO) with ISR and WO of the International Searching Authority, or the Declaration, PCT/GB2008/001437, mailed Sep. 9, 2008.

* cited by examiner

*Primary Examiner* — Suzanne Noakes
*Assistant Examiner* — Jae W Lee
(74) *Attorney, Agent, or Firm* — Hamilton, Brook, Smith & Reynolds, P.C.

(57) ABSTRACT

Protein lattices are disclosed which have a regular structure with a repeating unit repeating in three dimensions and have many uses, for example to support an array of macromolecular entities for X-ray crystallography. The repeating unit comprises protein protomers which each comprise at least two monomers fused together. The monomers are each monomers of a respective oligomer assembly into which the monomers are assembled for assembly of the protomers into the lattice. The repeating unit comprises protomers comprising at least a first monomer which is a monomer of a first oligomer assembly which has a set of rotational symmetry axes extending in three dimensions, and a further monomer fused to the first monomer which further monomer is a monomer of a further oligomer assembly which has a rotational symmetry axis of the same order as one of the set of rotational symmetry axes of the first oligomer assembly.

34 Claims, 3 Drawing Sheets

Unary Mixed Crysalin $p_4d_4$

Self-Assembly

Protomer $p_4d_4$

Gene Fusion

Assemblies O and $D_4$

Homologous O
Human Heavy Chain
Ferritin

Homologous $D_4$
*E.coli* PurE

SEQUENCE LISTING

<160> NUMBER OF SEQ ID NOS: 4

<210> SEQ ID NO 1
<211> LENGTH: 32
<212> TYPE: DNA
<213> ORGANISM: Homosapien

<400> SEQUENCE: 1
ccttagtcga attcatgacg accgcgtcca cc                32

<210> SEQ ID NO 2
<211> LENGTH: 33
<212> TYPE: DNA

-continued

```
<213> ORGANISM: Homosapien

<400> SEQUENCE: 2
gggaaattag ccctcgagtt agctttcatt atc                              33

<210> SEQ ID NO 3
<211> LENGTH: 33
<212> TYPE: DNA
<213> ORGANISM: E. coli

<400> SEQUENCE: 3
gttttaagac ccatggcttc ccgcaataat ccg                              33

<210> SEQ ID NO 4
<211> LENGTH: 30
<212> TYPE: DNA
<213> ORGANISM: E. coli

<400> SEQUENCE: 4
cgcaaacctg gatcctgccg cacctcgcgg                                  30
```

PROTEIN LATTICE

RELATED APPLICATION

This application is the U.S. National stage of International Application No. PCT/GB03/04306, filed Oct. 8, 2003, designating the United States, published in English, and claiming priority under 35 U.S.C. §119 to United Kingdom Application No. 0223323.7, filed Oct. 8, 2002. The entire teachings of the above applications are incorporated herein by reference.

The present invention relates to protein lattices having a regular structure repeating in three dimensions. The protein lattices are based on symmetrical oligomer assemblies capable of self-assembly from the monomers of the oligomer assembly. Such protein lattices may have pores with dimensions of the order of nanometers to hundreds of nanometers. As such, the protein lattices are nanostructures which have many potential uses, for example as a matrix to support macromolecular entities for X-ray crystallography.

WO-00/68248 discloses regular protein structures based on symmetrical oligomer assemblies capable of self-assembly. In particular, WO-00/68248 discloses structures formed from protein protomers (referred to as a "fusion protein" in WO-00/68248) comprising at least two monomers (referred to as "oligomerization domains" in WO-00/68248) which are each monomers of a respective symmetrical oligomer assembly. Self-assembly of the monomers into the oligomer assembly causes assembly of the regular structures themselves. Several different types of structures are disclosed, including discrete structures and structures extending in one, two and three dimensions.

In WO-00/68248, the relative orientations of the monomers within the protomers are selected to provide the desired regular structure upon self-assembly. The monomers are fused together through a rigid linking group which is carefully selected to provide the requisite relative orientation of the monomers in the protomer. For example, in the laboratory production reported in WO-00/68248, the selection of the protomer was performed using a computer program to model monomers connected by a linking group in the form of a continuous, intervening alpha-helical segment over a range of incrementally increased lengths. Thus, the lattices suggested in WO-00/68248 having a regular structure repeating in three dimensions are formed from protomers comprising two monomers of respective dimeric or trimeric oligomer assemblies which are symmetrical about a single rotational axis. The relative orientation of the two monomers is selected to provide a specific angle of intersection between the rotational symmetry axis of the two oligomer assemblies. Thus, there is a single fusion between the two oligomer assemblies and the relative orientation of the oligomer assemblies is controlled by careful selection of the linking group providing the fusion.

WO-00/68248 only reports laboratory production of protein structures of a discrete cage and a filament extending in one dimension. It is expected that application of the teaching of WO-00/68248 to protein lattices repeating in three dimensions would encounter the following difficulties. Firstly, it is expected that there would be a difficulty in design arising from the requirement to select the relative orientation of the monomers within the protomer appropriate for constructing a lattice. This would probably reduce the numbers of types of oligomer assembly available to form a protein lattice, and hence make it difficult to identify suitable proteins. Secondly, it is expected that practical difficulties would be encountered during assembly. The structures disclosed in WO-00/68248 rely on the rigidity of the fusion between monomers in protomers which forms the single fusion between oligomer assemblies. WO-00/68248 teaches that the relative orientation of the monomers in the protomers controls the relative orientation of the oligomer assemblies in the resultant structure, so it is expected that flexing of the fusion away from the desired relative orientation would reduce the reliability of self-assembly. It is expected that such a problem would become more acute as the size of the repeating unit increases, thereby providing a practical restriction on the reliable production of lattices with a relatively large pore sizes.

Accordingly, it would be desirable to provide protein lattices having a different type of structure in which these expected problems might be alleviated.

According to a first aspect of a present invention, there is provided a protein lattice having a regular structure with a repeating unit repeating in three dimensions, the repeating unit comprising protein protomers which each comprise at least two monomers fused together, the monomers each being monomers of a respective oligomer assembly into which the monomers are assembled for assembly of the protomers into the lattice, wherein the repeating unit comprises protomers comprising at least a first monomer which is a monomer of a first oligomer assembly which has a quaternary structure which is symmetrical in three dimensions.

As a result of using at least a first oligomer assembly which is symmetrical in three dimensions, the structure of the repeating unit and hence the protein lattice is derived from the symmetry of the oligomer assembly. In particular, it is not dependent on the relative orientation of the monomers within the protomer. Therefore, protein lattices in accordance with the present invention may be designed by selecting oligomers assemblies wherein at least the first oligomer assembly has an appropriate three dimensional symmetry to build a lattice repeating in three dimensions. Protomers are then produced comprising monomers of the selected oligomer assemblies fused together. Subsequently, the protomers are allowed to self-assemble under suitable conditions. As described in more detail below, the chosen symmetries of the oligomer assemblies cause the protomers to self-assemble into the protein lattice.

To assist in understanding, reference is made to FIG. 1 which illustrates a particular example of a protein lattice in accordance with the present invention, as described in more detail below. In particular, the protein lattice 1 has a regular structure with a repeating unit comprising a first oligomer assembly 3 which is symmetrical in three dimensions, which in this example is human heavy chain ferritin which has octahedral symmetry. Each of the monomers 5 of the first oligomer assembly 3 is fused to a further monomer 6 of a further oligomer assembly 4 which in this example is *E. Coli* PurE has symmetry belonging to the dihedral $D_4$ point group 4. The further monomers 6 are assembled into the further oligomer assemblies 4 arranged with their rotational symmetry axes of order 4 aligned along the rotational symmetry axes of order 4 of the first oligomer assembly 3. Thus, the symmetry of the repeating unit, and hence the symmetry of the protein lattice 1, is the same as the symmetry of the set of rotational symmetry axes of order 4, as will be described in more detail below.

Accordingly, the present invention involves the use of a different class of oligomers assemblies from that used in WO-00/68248 and provides the benefit that one is not restricted by the selection of the relative orientation of the monomers within the protomer. Thus it is expected that the design of protein lattice will be assisted in that the relative orientation of the monomers withing the protomer is a less critical constraint. Similarly, it is expected that more reliable assembly of the protein lattices will be possible, as described in more detail below.

According to other aspects of the present invention, there is provided an individual protomer or plural protomers capable of self-assembly to form such a protein lattice, as well as polynucleotides encoding such protomers, vectors and host cells capable of expressing such promoters and methods of making the protomers.

The present invention will now be described in more detail by way of non-limitative example with reference to the accompanying drawings in which.

Figure 1:
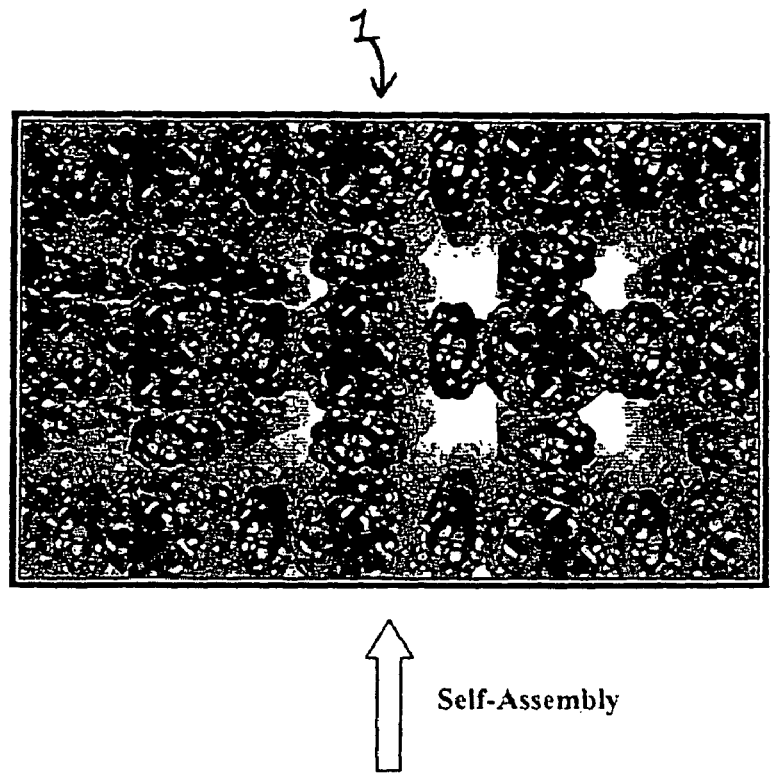
FIG. 1 is a diagram schematically illustrating, for a first protein lattice, the design of a homologous protomer based on two oligomer assemblies and production of the lattice itself.
Figure 1:
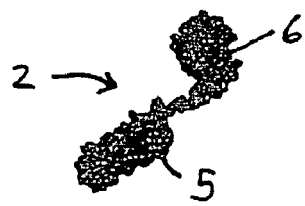
Figure 1:
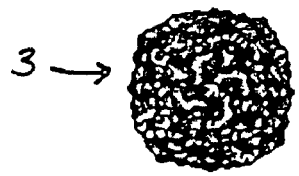
Figure 1:
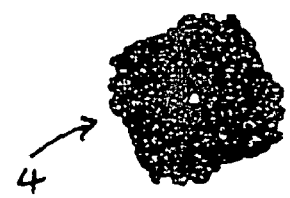

Protein lattices in accordance with the present invention may be designed by selecting oligomer assemblies, at least a first of which is symmetrical in three dimensions, which fused together produce a repeating unit which is capable of repeating in three dimensions. As the symmetry of the repeating unit, and hence the lattice as a whole, depends on the symmetry of the oligomer assemblies, this involves a selection of oligomer assemblies having a quaternary structure which provides appropriate symmetries. This is a straightforward task, because the symmetries of oligomer assemblies are generally available in the scientific literature on proteins, for example from The Protein Data Bank; H. M. Berman, J. Westbrook, Z. Feng, G. Gilliland, T. N. Bhat, H. Weissig, I. N. Shindyalov & P. E. Bourne; Nucleic Acids Research, 28 pp. 235-242 (2000) which is the single worldwide archive of structure data of biological macromolecules, also available through websites such as those described in The Protein Data Bank; H. M. Berman, J. Westbrook, Z. Feng, G. Gilliland, T. N. Bhat, H. Weissig, I. N. Shindyalov & P. E. Bourne; Nucleic Acids Research, 28 pp. 235-242 (2000).

In some lattices, the repeating unit repeats in the same orientation across the lattice. In other lattices two or more adjacent repeating units together form a unit cell which repeats in the same orientation across the lattice, but with the repeating units within a unit cell arranged in different orientations.

Examples of oligomer assemblies which produce lattices with a repeating unit repeating in three dimension are given below.

Advantageously, the first oligomer assembly has a quaternary structure with a set of rotational symmetry axes extending in three dimensions. As a result, said repeating unit includes protomers with the first monomers of the protomers being assembled into said first oligomer assembly and, in respect of respective ones of said set of rotational symmetry axes, with further monomers of the protomers fused to respective first monomers being arranged symmetrically around said respective one of said set of rotational symmetry axes.

The arrangement of the repeating unit, and hence the lattice as a whole, is therefore dependent on the symmetries of the first oligomer assembly. In particular, in the assembled first oligomer assembly, inevitably and by definition, there are groups of first monomers arranged symmetrically around each of the set of rotational symmetry axes of the first oligomer assembly. This is because the symmetry results from the identical monomers being so arranged around the rotational symmetry axes.

Since the further monomers are each fused to a respective first monomer, it follows that groups of the further monomers are also arranged symmetrically around each of the set of rotational symmetry axes. The further monomers are held in this symmetrical arrangement by being attached to first monomers in the first oligomer assembly. These groups of symmetrically arranged further monomers fused to the first oligomer assembly self-assemble with other monomers (which may be corresponding further monomers of another repeating unit, or may be monomers in a different part of the same unit cell) to form further oligomer assemblies, which are also arranged symmetrically around the set of rotational symmetry axes of the first oligomer assembly.

Thus, the arrangement of the repeating unit, and hence the lattice as a whole, is dependent on the symmetries of the first oligomer assembly, not on the relative orientation of the monomers within an individual protomer. In other words, the present invention provides the advantage that the three dimensional structure of the protein lattice may be based solely on the symmetries of the oligomer assemblies. This provides advantages in the design of the protein lattices. This is to say, the design of the repeating unit and hence the lattice as a whole may be based on the symmetries of the oligomer assemblies. This makes it easy to select appropriate oligomer assemblies for use in the protein lattice.

Desirably, the first oligomer assembly has a quaternary structure with a set of rotational symmetry axes extending in three dimensions, and, in said protomers, further monomers fused to said first monomers are monomers of respective further oligomer assemblies which have a rotational symmetry axis of the same order as a respective one of said set of rotational symmetry axes of said first oligomer assembly. As a result, said repeating unit includes protomers with the first monomers of the protomers being assembled into said first oligomer assembly and, in respect of respective ones of said set of rotational symmetry axes, with further monomers of the protomers fused to respective first monomers being assembled into respective further oligomer assemblies with said rotational symmetry axis of said respective further oligomer assemblies being aligned with the respective rotational symmetry axis of said first oligomer assembly.

The arrangement of the repeating unit and hence the lattice as a whole are therefore dependent on the symmetries of the first and further oligomer assemblies. In particular, as described above, in the first oligomer assembly there are groups of first monomers arranged symmetrically around each of the set of rotational symmetries axes, which in turn result in groups of the further monomers fused to the first monomers also being arranged symmetrically around each of the set of rotational symmetry axes of the first oligomer assembly. These groups of symmetrically arranged further monomers fused to the first oligomer assembly self-assemble with other monomers to form the further oligomer assembly. The further monomers may be further monomers of another repeating unit or may be monomers in a different part of the same repeating unit.

As a result of the further monomers fused to the first oligomer assembly being arranged symmetrically around a rotational symmetry axis of the first oligomer assembly, it follows that the further oligomer assembly is held with the group of fused further monomers also held symmetrically around that rotational symmetry axis of the first oligomer assembly. However, inevitably and by definition, the further monomers also assemble in the further oligomer assembly in a symmetrical arrangement around the rotational symmetry axis of the further oligomer assembly. Thus, the result of the further oligomer assembly having a rotational symmetry axis of the same order as one of the set of rotational symmetry axes of the first oligomer assembly is that the first and further oligomer assemblies assemble with their symmetry axes aligned with one another. It follows from the symmetry of both oligomer assemblies that this is the most stable arrangement. This results in an N-fold fusion between the first and further oligomer assemblies, where N is a plural number equal to the order of the respective rotational symmetry axis of the first oligomer assembly and the rotational symmetry axis of the further oligomer assembly. In each of the first and further oligomer assemblies, there are N monomers arranged around the rotational symmetry axis, each of the monomers being fused within a respective protomer to a monomer of the other oligomer assembly.

Thus the set of rotational symmetry axes does not include all the rotational symmetry axes of the first oligomer assembly. Rather the set comprises the rotational symmetry axes of the first oligomer assembly which are of the same order as rotational symmetry axes of the further oligomer assembly. For example in the example of FIG. 1, the set of rotational symmetry axes of the first oligomer assembly 3 are the rotational symmetry axes of order 4, rather than those of order 3 or 2, due to the further oligomer assembly 4 having rotational symmetry axes of order 4. Further examples are given below.

The particular choice of symmetries of the first and further oligomer assemblies results, on assembly of the protomers into the lattice, in the oligomer assemblies being built up with their rotational symmetry axes aligned. This means that the arrangement of the repeating unit, and hence the lattice as a whole, is controlled by the symmetries of the first and further oligomer assemblies, not on the relative orientation of the monomers within an individual protomer. In other words, the present invention provides the advantage that the three dimensional structure of the protein lattice may be based solely on the symmetries of the oligomer assemblies. This is advantageous in the design of the protein lattice. By basing the three dimensional structure of the repeating unit and hence lattice as a whole, on the symmetries of the oligomer assemblies, it is easier to select appropriate oligomer assemblies to form a lattice. During design, the relative orientation of the monomers within an individual protomer in its unassembled form becomes a much lower constraint than is present in, for example, WO-00/68248.

There are also expected to be advantages during self-assembly of the lattice. In particular, the formation of an N-fold fusion between two given oligomer assemblies results in the bond between the two oligomer assemblies being relatively rigid. This is expected to reduce relative motion of the oligomer assemblies during the assembly process. This is expected to assist in reliable formation of the lattice with the oligomer assemblies in the correct relative positions.

Although there are particular advantages in the use of a further oligomer assembly which has a rotational symmetry axis of the same order as the rotational symmetry axes of the first oligomer assembly, this is not essential. Alternatively, it would be possible for the further monomers arranged symmetrically around the rotational symmetry axes of the first oligomer assembly to be monomers of separate oligomer assemblies, for example of dimeric oligomer assemblies (being heterologous or homologous). In that case, the further oligomer assembly would effectively be replaced by a group of separate dimeric oligomer assemblies, equal in number to the order of the rotational symmetry axis of the first oligomer assembly, with the separate dimeric oligomer assemblies held around the rotational symmetry axis of the first oligomer assembly in an arrangement which might or might not have the N-fold symmetry of the rotational symmetry axis of the first oligomer assembly.

The form and production of the protomers will now be described. Except that the present invention involves protomers in which a different choice of monomers from WO-00/68248 are fused together, the form and production of the protomers per se, as well as the polynucleotide encoding the protomers, may be as the same as disclosed in WO-00/68248 which is therefore incorporated herein by the reference.

The nature of the monomers themselves will now be described.

The monomers are monomers of oligomer assemblies which are capable of self-assembly under suitable conditions to produce a protein lattice. The secondary and tertiary structure of the monomers is unimportant in itself providing they assemble into a quaternary structure with the required symmetry. However, it is advantageous if the protein is easily expressed and folded in an heterologous expression system (for example using plasmid expression vector in *E. Coli*).

The monomers may be naturally occurring proteins, or may be modified by peptide elements being absent from, substituted in, or added to a naturally occurring protein provided that the modifications do not substantially affect the assembly of the monomers into their respective oligomer assembly. Such modifications are in themselves known for a number of different purposes which may be applied to monomers of the present invention. In other words, the monomer may be a homologue and/or fragment and/or fusion protein of a naturally occurring protein.

The monomer may be chemically modified, e.g. post-translationally modified. For example, it may be glycosylated or comprise modified amino acid residues.

The monomers are preferably fused genetically, although in principle other fusions are possible such as chemical fusions.

Although the monomers may be fused directly together, preferably the monomers are fused by a linking group of peptide or non-peptide elements. In general, linking two proteins by a linking group is known for other purposes and such linking groups may be applied to the present invention.

Another factor in the selection of appropriate oligomer assemblies is the location and orientation of (a) the termini of the first monomers when arranged in the first oligomer assembly in its natural form (i.e. not fused to a further oligomer assembly) and (b) the termini of the further monomers when arranged in the further oligomer assembly in its natural form (i.e. not fused to the first oligomer assembly). Such information on the arrangement of the termini in the oligomer assembly in its natural form is generally available for oligomer assemblies, for example from The Protein Data Bank referred to above. Ideally, these termini should have the same separation and orientation, because they will be fused together in the assembled protein lattice to constitute the N-fold fusion arranged symmetrically around a rotational symmetry axis. That being said, it is not essential for the separation and orientation to be the same, because any difference may be accommodated by deformation of the monomers near the N-fold fusion and/or by use of a linking group. Therefore, as a general point, oligomer assemblies should be chosen in which the termini of both oligomer assemblies which are to be fused together in an N-fold fusion allows formation of the fusion without preventing assembly of the oligomer assemblies and hence the protein lattice.

Considering the deformation of the monomers near the N-fold fusion mentioned above, it is desirable to minimise such deformation which will tend to reduce the reliability of the assembly process. However, if a linking group is fused between the monomers, such deformation may be taken up, at least partially, by the linking group itself. This reduces the deformation of the monomers, thereby increasing the reliability of self-assembly because the linking group does not take part in the assembly process as regards to not being part of the naturally occurring protein. There is a particular advantage of the use of a linking group.

Furthermore, the linking group may be specifically designed to be oriented relative to the first and further monomers in the protomer in its normal form, prior to assembly, to reduce such differences in the position and/or orientation of the termini of the first and further monomers. Using position and orientation of the termini of the first and further monomers in the first and further oligomer assemblies in their natural form which is generally available for oligomer assemblies, as discussed above, it is possible to design an appropriate linking group using conventional modelling techniques.

Typically, the monomers are fused at their end termini. Alternatively, the monomers may be fused at an alternative location in the polypeptide chain so long as the native fold and symmetry of the naturally occurring oligomer assembly remains the same. For example, one of the monomers may be inserted into a structurally tolerant portion of the other monomer, for example in a loop extending out of the oligomer assembly. Also, truncation of a monomer is feasible and may be estimated by structural examination.

Some examples of symmetries for the oligomer assemblies to produce a protein lattice are as follows.

In the examples, the first oligomer assembly which is symmetrical in three dimensions belongs to one of a tetrahedral point group, an octahedral point group or a dihedral point group.

In some classes of protein lattice, the protomers are homologous with respect to the monomers, ie there is a single type of protomer within the protein lattice. For example, Table 1 represents some simple homologous protomers capable of forming a protein lattice.

TABLE 1

Homologous Protomers

| Protomer | Class Name | M | N |
|---|---|---|---|
| $p_3p_3$ | Platonic | 12 | 3 |
| $p_4p_4$ | Platonic | 24 | 4 |
| $p_4p_3$ | Platonic | 24 | 3 (or 12) |
| $p_3d_3$ | Mixed | 12 | 3 |
| $p_3d_2$ | Mixed | 12 | 2 |
| $p_4d_4$ | Mixed | 24 | 4 |
| $p_4d_3$ | Mixed | 24 | 3 |
| $p_4d_2$ | Mixed | 24 | 2 |
| $d_3d_3d_2$ | Dihedral | 6 | 3, 2 |
| $d_4d_4d_2$ | Dihedral | 8 | 4, 2 |
| $d_6d_6d_2$ | Dihedral | 12 | 6, 2 |

In Table 1, each protomer is identified by letters which represent the respective monomers of the protomer. In particular the letters identify the point group to which the oligomer assembly of that monomer belongs. For each letter, the subscript number represents the order of the point group. The letter p represents a platonic point group, so $p_3$ represents a tetrahedral point group, and $p_4$ represents an octahedral point group. The letter d represents a dihedral point group.

In the final two columns of the table, there is given the number M of first monomers in the first oligomer assembly and the order(s) N of the set of rotational symmetry axes of the first oligomer assembly. N is also the order of the rotational symmetry axis of the further oligomer assembly aligned with a respective rotational symmetry axis of the first oligomer assembly, and around which there is formed an N-fold fusion between the first and further oligomer assemblies.

The protomers have been divided into classes which have been named according to the nature of the monomers of the proteins for ease of reference.

In both the platonic and mixed classes, the first oligomer assembly belongs to a platonic point group, which is either a tetrahedral point group or an octahedral point group.

In the mixed class, the further monomer is a monomer of an oligomer assembly belonging to a dihedral point group. In each case, the order N of the dihedral point group, which is the order of the principal rotational symmetry axis of the dihedral point group, is equal to the order of one of the rotational symmetry axes of the first oligomer assembly. This may either be the principal rotational symmetry axis of the first oligomer assembly or one of the rotational symmetry axes of the first oligomer assembly of lower order. The rotational symmetry axes of the first oligomer assembly of order N therefore constitute the set of rotational symmetry axes of the first oligomer assembly. The symmetries of the first and further oligomer assemblies results in the formation of a unit cell in which the principal rotational symmetry axis of each further oligomer assembly belonging to a dihedral point group is aligned with one of set of rotational symmetry axes of order N of the platonic point group, with an N-fold fusion therebetween, in the manner described above.

The protein lattices of the mixed class are the easiest to visualise. In particular, the first oligomer assembly belonging to a platonic point group may be visualised as a node from which the set of rotational symmetry axes of order N extend outwardly. The dihedral point groups may be visualised as linear links with the principal rotational symmetry axis of the dihedral point group aligned with one of the set of rotational symmetry axes of order N of the first oligomer assembly. In this way, it is easy to visualise the formation of the lattice with pores in the spaces between the oligomer assemblies.

FIG. 1 illustrates a particular example of a protein lattice 1 belonging to the mixed class, in particular having a protomer 2 represented by $p_4d_4$. The first oligomer assembly 3 is human ferritin heavy chain (HFH) which belongs to an octahedral point group. The further oligomer assembly is E. Coli PurE which belongs to a dihedral $D_4$ point group of order 4. The protomer comprises a first monomer 5 of the first oligomer assembly 3 and a further monomer 6 of the further oligomer assembly 4 fused together. On assembly, the protomers 2 form a lattice 1 in which the repeating unit (which is also a unit cell) may be taken as, for example, one of the first oligomer assemblies 3, together with and half of each of the adjacent second oligomer assemblies 4 formed by the further monomers 6 fused to the first monomers 5 of that first oligomer assembly 1. Clearly visible from FIG. 1 is the symmetry of the protein lattice 1 based on the symmetries of the first oligomer assembly 3 and the further oligomer assembly 4. In particular as the rotational symmetry axes of order 4 of the further oligomer assembly 4 are aligned with the set of rotational symmetry axes of order 4 of the first oligomer assembly 3 the symmetry of the lattice is the same as the symmetry of the set of rotational symmetry axes.

In the platonic class, the further oligomer assembly belongs to a platonic point group as well as the first oligomer assembly.

In the first two protein lattices where the protomers belong to platonic point groups of the same order, the first and further oligomer assemblies may be identical, in which case the first and further monomers are also identical, or may be different oligomer assemblies belonging to an identical point group. The set of rotational symmetry axes of order N around which is formed an N-fold fusion are the principal rotational symmetry axes of the two oligomer assemblies.

In the third protein lattice in the platonic class where the first and further oligomer assemblies belong respectively to tetrahedral and octahedral point groups (or vice versa), the rotational symmetry axes of order N around which the N-fold fusion occurs are the rotational symmetry axes of order 3 of the two oligomer assemblies. In this case, either one of the oligomer assemblies may be considered as the first oligomer assembly. If the oligomer assembly belonging to a tetrahedral point group is considered as the first oligomer assembly, then the set of rotational symmetry axes are the principal rotational symmetry axes. If the oligomer assembly belonging to an octahedral point group is considered as the first oligomer assembly, then the set of rotational symmetry axes are the set of rotational symmetry axes of order 3, because this is the order of the rotational symmetry axes of the further oligomer assembly belonging to the tetrahedral point group.

The platonic class may be visualised by considering each oligomer assembly as a node from which the set of rotational symmetry axes of order N extend outwardly and joined to the rotational symmetry axes of an oligomer assembly of the opposite type.

Lastly, in the dihedral class, the protomers comprise three monomers all belonging to a dihedral point group. The central monomer may be considered as the first monomer of a first oligomer assembly belonging to a dihedral point group of order 3, 4 or 6. The monomers fused to each terminus of the first oligomer assembly may each be considered as the further monomers. One of the further monomers is a monomer of a further oligomer assembly belonging to a dihedral point group of the same order as the dihedral point group of the first oligomer assembly. Thus, as a result of the symmetries of the first oligomer assembly and this one of the further oligomer assembly, this results of the formation of a repeating unit in which the principal rotational symmetry axes of both oligomer assemblies (i.e. the rotational symmetry axis of the same order as the dihedral point group) are aligned. Therefore, in the protein lattice, these oligomer assemblies are arranged in columns along which the first and further oligomer assemblies are alternately arranged.

The other of the further monomers is a monomer of an oligomer assembly belonging to a dihedral point group of order 2 and so have a rotational symmetry axis of order 2 which is equal to the rotational symmetry axis of order 2 of the first oligomer assembly. Such rotational symmetry axes of the first oligomer assembly are equal in number to the order of the dihedral point group to which the first oligomer assembly belongs, and extend perpendicular to the principal rotational symmetry axis of the dihedral point group, being arranged symmetrically around that principal rotational symmetry axis. Therefore, the further oligomer assemblies belonging to a dihedral point group of order 2 are arranged in the assembled protein lattice with their principal rotational symmetry axes aligned to the just described rotational symmetry axes of order 2 of the first oligomer assembly. As these extend perpendicular to the principal rotational symmetry axes of the first oligomer assembly, the further oligomer assemblies belonging to a dihedral point group of order 2 may be considered as links between the columns of oligomer assemblies described above.

In other words, the set of rotational symmetry axes of the first oligomer assembly includes the principal rotational symmetry axis of order 3, 4 or 6, together with the rotational symmetry axes of order 2 perpendicular to the principal rotational symmetry axis.

In other classes of protein lattice, the protomers are heterologous with respect to the monomers i.e. there are two or more types of protomer in the protein lattice. To achieve assembly of any two types of protomer, the two types of protomer include different monomers of the same heterologous oligomer assembly. Thus when the protomers of the different types are allowed to assemble, the heterologous oligomer assemblies assemble, thereby linking the protomers of the two types. However, in contrast to homologous protomers, a single type of protomer cannot by itself assemble into the entire protein lattice. The individual monomers of the heterologous oligomer assembly cannot self-assemble into the entire heterologous oligomer assembly in the absence of the other, different monomers of that heterologous assembly. This provides advantages during manufacture of the protein lattices, because each type of protomer may be separately produced without assembly of an entire protein lattice which might otherwise disrupt the production of the protomer. This allows production in a two-stage process, which will be described in more detail below.

Preferably, the heterologous oligomer assembly belongs to a cyclic point group. In this case, the heterologous oligomer assembly may constitute a further oligomer assembly which is fused in the assembled lattice by an N-fold fusion to the first oligomer assembly.

In the simplest types of protein lattice, the heterologous protomers each further comprise a monomer of a homologous oligomer assembly, which may be the first oligomer assembly. The individual types of protomer may assemble into a respective, discrete component of the unit cell, as a result of the monomers of the homologous oligomer assembly self-assembling. This is an advantage of the heterologous protomers, because assembly of the lattice may be avoided until the components are brought together. Otherwise assembly of the lattice might hinder the production of the protomers themselves.

For example, Table 2 represents some simple heterologous protomers capable of forming a protein lattice.

TABLE 2

| | | Heterologous Protomers | | | | |
|---|---|---|---|---|---|---|
| | Compo- | | 1st Protomer | | 2nd Protomer | |
| Protomer | nents | Name | M | N | M | N |
| $p_3c_{3,4}$ + $p_3c_{3,4}$* | $P_3/P_3$ | Platonic | 12 | 3 | 12 | 3 |
| $p_4c_{3,4}$ + $p_3c_{3,4}$* | $P_4/P_4$ | Platonic | 24 | 3 | 12 | 3 |
| $p_4c_{3,4}$ + $p_3c_{3,4}$* | $P_4/P_3$ | Platonic | 24 | 3 | 12 | 3 |
| $p_3c_{3,4}$ + $d_3c_{3,4}$* | $P_3/D_3$ | Mixed | 12 | 3 | | |
| $p_3c_{2,4}$ + $d_2c_{2,4}$* | $P_3/D_2$ | Mixed | 12 | 2 | | |
| $p_4c_{4,4}$ + $d_4c_{4,4}$* | $P_4/D_4$ | Mixed | 24 | 4 | | |
| $p_4c_{3,4}$ + $d_3c_{3,4}$* | $P_4/D_3$ | Mixed | 24 | 3 | | |
| $p_4c_{2,4,3,4}$ + $d_2c_{2,4}$* | $P_4/D_2$ | Mixed | 24 | 2 | | |
| $c_{3,4}d_3d_2$ + $c_{3,4}$*$d_3d_2$ | $D_3/D_3$ | Dihedral | 6 | 3, 2 | 6 | 3, 2 |
| $c_{4,4}d_4d_2$ + $c_{4,4}$*$d_4d_2$ | $D_3/D_3$ | Dihedral | 8 | 4, 2 | 8 | 4, 2 |

TABLE 2-continued

Heterologous Protomers

| Protomer | Components | Name | 1st Protomer M | 1st Protomer N | 2nd Protomer M | 2nd Protomer N |
|---|---|---|---|---|---|---|
| $c_{6A}d_6d_2 + c_{6A}*d_6d_2$ | $D_6/D_6$ | Dihedral | 12 | 6, 2 | 12 | 6, 2 |
| $d_3d_3c_{2A} + d_3d_3c_{2A}*$ | $D_3/D_3$ | Dihedral | 6 | 3, 2 | 6 | 3, 2 |
| $d_4d_4c_{2A} + d_4d_4c_{2A}*$ | $D_4/D_4$ | Dihedral | 8 | 4, 2 | 8 | 4, 2 |
| $d_6d_6c_{2A} + d_6d_6c_{2A}*$ | $D_6/D_6$ | Dihedral | 12 | 6, 2 | 12 | 6, 2 |
| $c_{3A}d_3c_{2B} + c_{3A}*d_3c_{2B}*$ | $D_3/D_3$ | Dihedral | 6 | 3, 2 | 6 | 3, 2 |
| $c_{4A}d_4c_{2B} + c_{4A}*d_4c_{2B}*$ | $D_4/D_4$ | Dihedral | 8 | 4, 2 | 8 | 4, 2 |
| $c_{6A}d_6c_{2B} + c_{6A}*d_6c_{2B}*$ | $D_6/D_6$ | Dihedral | 12 | 6, 2 | 12 | 6, 2 |

In Table 2, monomers of a single heterologous oligomer assembly belonging to a cyclic point group are used so that the protein lattice is formed from two types of protomer identified in the first column. Each of the protomers includes one of the monomers of the heterologous oligomer assembly.

In Table 2, the monomers of each protomer are identified by lower case letters in similar manner as in Table 1. The lower case letters p and d have the same meaning as in Table 1. In addition, lower case c represents a monomer of a heterologous oligomer assembly belonging to a cyclic point group. The subscript number again represents the order of the point group. The subscript capital letters A and A* are used to identify the two different monomers of the same heterologous assembly.

In Table 2, the second column identifies the point groups to which the components resulting from the assembly of each type of protomer belongs. A similar notation is used as for the monomers of the protomer, except that capital letters are used to indicate that the point group of the component is being referred to. Thus capital letter P indicates that the component belongs to a platonic point group, so $P_3$ represents a tetrahedral point group and $P_4$ represents an octahedral point group. Capital letter D indicates that the component belongs to a dihedral point group. In a similar manner to Table 1, the final columns give, in respect of each protomer where appropriate, the number M of monomers in the first oligomer assembly and the order(s) N of the set of rotational symmetry axes of the first oligomer assembly which are aligned with the rotational symmetry axis of a further oligomer assembly.

For ease of reference, the protein lattices are divided into classes on the basis of the symmetry of their components, in a similar manner to the division of the protein lattices formed from homologous protomers. In each case, the heterologous protomers may be derived from the protomers of the corresponding class of homologous protomer in Table 1.

For the mixed class and the platonic class, the two types of protomers both comprise:
(a) a monomer of a homologous oligomer assembly which belongs to the same point group as a respective one of the monomers of the corresponding homologous protomer; and
(b) a monomer which is a respective one of the two different monomers of the heterologous oligomer assembly which belongs to a cyclic point group.

The order of the cyclic point group to which the heterologous oligomer assembly belongs is the same as the order N of the N-fold fusion between the oligomer assemblies of the protein lattice formed from the corresponding homologous protomer, that is the order of the respective rotational symmetry axis of the first oligomer assembly.

Thus, in the assembled protein lattice, the repeating unit has fundamentally the same arrangement as the repeating unit of the corresponding homologous protomer, except as follows. Instead of the N-fold fusion between the two homologous oligomer assemblies of the homologous protomer, the link between the homologous oligomer assemblies is extended by the insertion of the heterologous oligomer assembly. Therefore, it will be seen that the repeating unit of the heterologous oligomer assembly effectively extends the length of the links of the repeating unit between the first oligomer assemblies which may be considered as notes in the protein lattice. Thus, the size of the pores within the protein lattice is also increased relative to the use of the corresponding homologous protomers. Increasing the size of the pores in this manner represents a significant advantage of the use of heterologous protomers.

Figure 2:
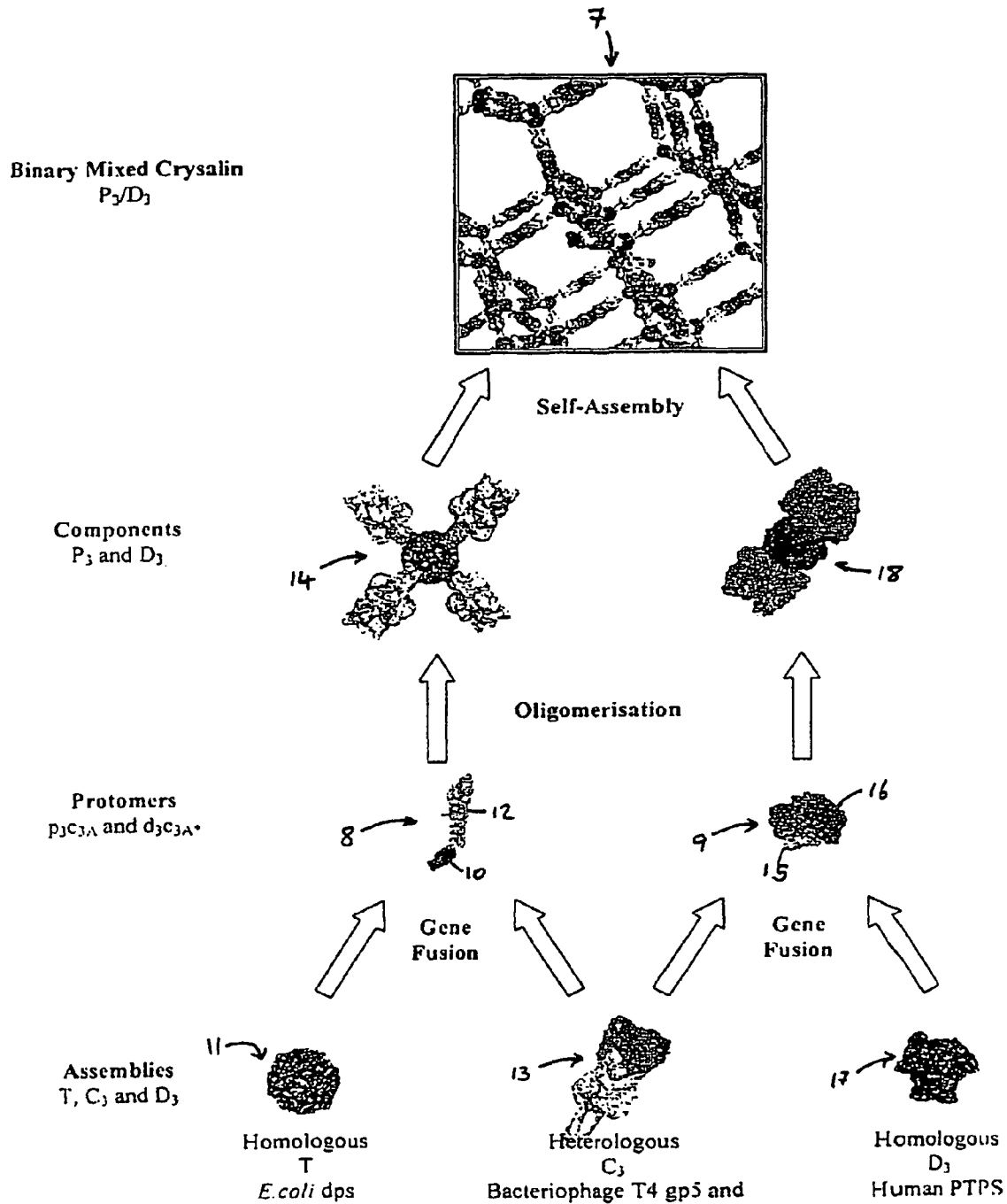
FIG. 2 is a diagram schematically illustrating, for a second protein lattice, the design of two heterologous protomers based on three oligomer assemblies and production of the lattice itself.

FIG. 2 illustrates a particular example of a protein lattice 7 belonging to the mixed class, in particular having respective protomers 8 and 9 represented by $p_3c_{3A}$ and $d_3c_{3A}*$, respectively. The first protomer 8 comprises a first monomer 10 of a first homologous oligomer assembly 11, namely is E. Coli dps which belongs to a tetrahedral point group. Fused to the first monomer 10 in the first protomer 8 is a further monomer 12 of a further heterologous oligomer assembly 13, namely bacteriophage T4 gp5 and gp27 which belongs to a cyclic point group of order 3. On assembly, the first protomer 8 forms a first component 14 by the first monomers 10 assembling together. The first component 14 has the same symmetry as the first oligomer assembly 11 of the first protomer 8.

The second protomer 9 comprises a monomer 15 which is the other monomer of the further oligomer 13 of the first protomer 8 which is heterologous to the further monomer 12 of the first protomer 8. The second protomer 9 also comprises a monomer 16 which is a monomer of a homologous oligomer assembly 17, namely human PTPS which belongs to a dihedral $D_3$ point group of order 3. On assembly, the second protomer 9 forms a second component 18 by the homologous monomers 16 assembling together.

When the first and second components 14 and 18 are brought together, they assemble to form the protein lattice 7 by assembly of the heterologous oligomer assembly 13. It is clearly visible from FIG. 2 how the symmetry of the protein lattice 7 is based on the symmetries of the homologous oligomer assemblies 11 and 17. In particular, the rotational symmetry axes of order 3 of both the heterologous oligomer assembly 13 and the homologous oligomer assembly 17 of the second protomer 9 are aligned with the set of rotational symmetry axes of order 3 of the first oligomer assembly 11 of the first protomer 8. It is further clear from FIG. 2 how the heterologous oligomer assemblies 13 effectively extend the length of the links between the first oligomer assemblies 11. In the lattice 7, the repeating unit may be taken, for example, as one of the first components 14 and half of each of the adjacent second components 18. In this case, the unit cell is formed by a number of such repeating units combined together.

The protomers of the dihedral class of the heterologous comprise protomers comprising three monomers which may be derived from a corresponding one of the dihedral class of homologous protomers. In particular, the two types of protomer comprise the corresponding homologous protomer with either one (or both) of the further monomers of the corresponding homologous protomers replaced by respective monomers of a heterologous oligomer assembly belonging to a cyclic point group of the same order as the dihedral point group to which the oligomer assembly of the replaced monomer belongs.

The above examples of protein lattices are believed to represent the simplest form of protomers capable of forming a protein lattice and are preferred for that reason. However, it will be appreciated that other protomers formed from monomers of oligomer assemblies having suitable symmetries will be capable of forming a protein lattice. For example, other homologous protomers having larger numbers of monomers than listed in Table 1 will be capable of forming a protein lattice. Similarly, other heterologous protomers will be capable of forming a protein lattice. These may include two types of protomer having larger numbers of monomers than in the examples of Table 2, or may include more than two types of protomer.

For each of the monomers, there is a large choice of oligomer assemblies having the required symmetry. The present invention is not limited to particular oligomer assemblies, because in principle any oligomer assembly having a quaternary structure with the requisite symmetry may be used. However, as examples Table 3 lists some possible choices of oligomer assembly for each of the point groups of Tables 1 and 2.

TABLE 3

Example oligomer assemblies

| Point Group | Source | Name of Oligomer Assembly | PDB Code |
|---|---|---|---|
| $P_3(T, 32)$ | E. coli | dps | 1DPS |
| | S. epidermis | EpiD | 1G63 |
| $P_4(O, 432)$ | Human | heavy chain ferritin | 2FHA |
| | E. coli | Dihydrolipoamide succinyltransferase | 1E2O |
| | A. vinelandii | Dihydrolipoamide acetyltransferase | 1EAB |
| $D_2$ | Human | Mn superoxide dismutase | 1AP5 |
| | P. falciparum | lactate dehydrogenase | 1CEQ |
| $D_3$ | Rat | 6-pyruvoyl tetrahydropterin synthase | 1B66 |
| | E. coli | Amino acid aminotransferase | 1I1L |
| $D_4$ | E. coli | PurE | 1QCZ |
| | Sipunculid worm | Hemerythrin | 2HMQ |
| $D_6$ | S. typhimurium | Glutamine Synthetase | 1F1H |
| $C_{2A} + C_{2A}^*$ | Human | Casein kinase alpha and beta chains | 1JWH |
| $C_{3A} + C_{3A}^*$ | Coliphate T4 | gp5 + gp27 | 1K28 |
| | HIV | N36 + C34 | 1AIK |
| | Pseudomonas putida | Napthalene 1,2-Dioxygenase | 1NDO |
| $C_{4A} + C_{4A}^*$ | Erachiopod | Hemerythrin | N/A |

Thus the present invention provides a protein protomer or plural protein protomers capable of assembly into a protein lattice. The monomers of the protomer may be of any length but typically have a length of 5 to 1000 amino acids, preferably at least 20 amino acids and/or preferably at most 500 amino acids.

The invention also provides polynucleotides which encode the protein protomers of the invention. The polynucleotide will typically also comprise an additional sequence beyond the 5 and/or 3 ends of the coding sequence. The polynucleotide typically has a length of at least three times the length of the encoded protomer. The polynucleotide may be RNA or DNA, including genomic DNA, synthetic DNA or cDNA. The polynucleotide may be single or double stranded.

The polynucleotides may comprise synthetic or modified nucleotides, such as methylphosphonate and phosphorothioate backbones or the addition of acridine or polylysine chains at the 3' and/or 5' ends of the molecule.

Such polynucleotides may be produced and used using standard techniques. For example, the comments made in WO-00/68248 about nucleic acids and their uses apply equally to the polynucleotides of the present invention.

The monomers are typically combined to form protomers by fusion of the respective genes at the genetic level (e.g. by removing the stop codon of the 5' gene and allowing an in-frame read through to the 3' gene). In this case the recombinant gene is expressed as a single polypeptide. The genes may, alternatively, be fused at a position other than the end terminus so long as the quaternary structure of the oligomer assembly properties remains substantially unaffected. In particular, one gene may be inserted within a structurally tolerant region of a second gene to produce an in-frame fusion.

Chemical fusion of the polypeptide chains may be used as an alternative to fusion at the genetic level. In this instance the polypeptides are fused post-translationally by means of the covalent linkage, but in particular through the use of intein chemistry.

The invention also provides expression vectors which comprise polynucleotides of the invention and which are capable of expressing a protein protomer of the invention. Such vectors may also comprise appropriate initiators, promoters, enhancers and other elements, such as for example polyadenylation signals which may be necessary, and which are positioned in the correct orientation, in order to allow for protein expression.

Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be for example, plasmid, virus or phage vector. Typically the vector has an origin of replication. The vector may comprise one or more selectable marker genes, for example an ampicillin resistance gene in the case of a bacterial plasmid or a resistance gene for a fungal vector.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters include the metallothionein promoter which can be induced in response to heavy metals such as cadmium. Viral promoters such as the SV40 large T antigen promoter or adenovirus promoters may also be used.

Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR).

Another method that can be used for the expression of the protein protomers is cell-free expression, for example bacterial, yeast or mammalian.

The invention also includes cells that have been modified to express the protomers of the invention. Such cells include transient, or preferably stable higher eukaryotic cell lines, such as mammalian cells or insect cells, using for example a baculovirus expression system, lower eukaryotic cells, such as yeast or prokaryotic cells such as bacterial cells. Particular examples of cells which may be modified by insertion of vectors encoding for a polypeptide according to the invention include mammalian HEK293T, CHO, HeLa and COS cells. Preferably the cell line selected will be one which is not only stable, but also allows for mature glycosylation of a polypeptide. Expression may be achieved in transformed oocytes.

The protein protomers, polynucleotides, vectors or cells of the invention may be present in a substantially isolated form. They may also be in a substantially purified form, in which case they will generally comprise at least 90%, e.g. at least 95%, 98% or 99%, of the proteins, polynucleotides, cells or dry mass of the preparation.

The protomers may be prepared using the vectors and host cells using standard techniques. For example, the comments made in WO-00/68248 regarding methods of preparing protomers (referred to as "fusion proteins" in WO-00/68248) apply equally to preparation of protomers according to the present invention.

Assembly of the protein lattice from the protomers may be performed simply by placing the protomers under suitable conditions for self-assembly of the monomers of the oligomer assemblies. Typically, this will be performed by placing the protomers in solution, preferably an aqueous solution. Typically, the suitable conditions will correspond to those in which the naturally occurring protein self-assembles in nature. Suitable conditions may be those specifically disclosed in WO-00/68248.

In the case of homologous protomers this results in direct assembly of the protein-lattice.

In the case of heterologous protomers, assembly is preferably performed in plural stages. In a first stage, each type of protomer is separately assembled into a respective discrete component. In a second stage, the discrete components are brought together and assembled into the protein lattice. Where plural heterologous protomers are used, there may be further stages intermediate the first and second stage in which the respective discrete components are brought together and assembled into larger, intermediate components.

A specific protein lattice of the type illustrated in FIG. 1 has been prepared using the following method.

Human ferritin heavy chain (HFH) and the *E. coli* PurE genes were amplified by PCR from human cDNA and *E. coli* gDNA respectively. Primers for amplification of the ferritin gene were: 5'-CCT TAG TCG AAT TCA TGA CGA CCG CGT CCA CC-3' (SEQ ID NO:1) and 5'-GGG AAA TTA GCC CTC GAG TTA GCT TTC ATT ATC-3' (SEQ ID NO:2). Primers for amplification of the PurE gene were: 5'-GTT TTA AGA CCC ATG GCT TCC CGC AAT AAT CCG-3' (SEQ ID NO:3) and 5'-CGC AAA CCT GGA TCC TGC CGC ACC TCG CGG-3' (SEQ ID NO:4). The PurE gene was cloned into the pET-28b vector (Novagen) between the NcoI and BamHI sites. The HFH gene was cloned into the resulting vector between the EcoRI and XhoI sites to create an in-frame fusion of the two genes under control of the T7lac promoter.

Figure 3:
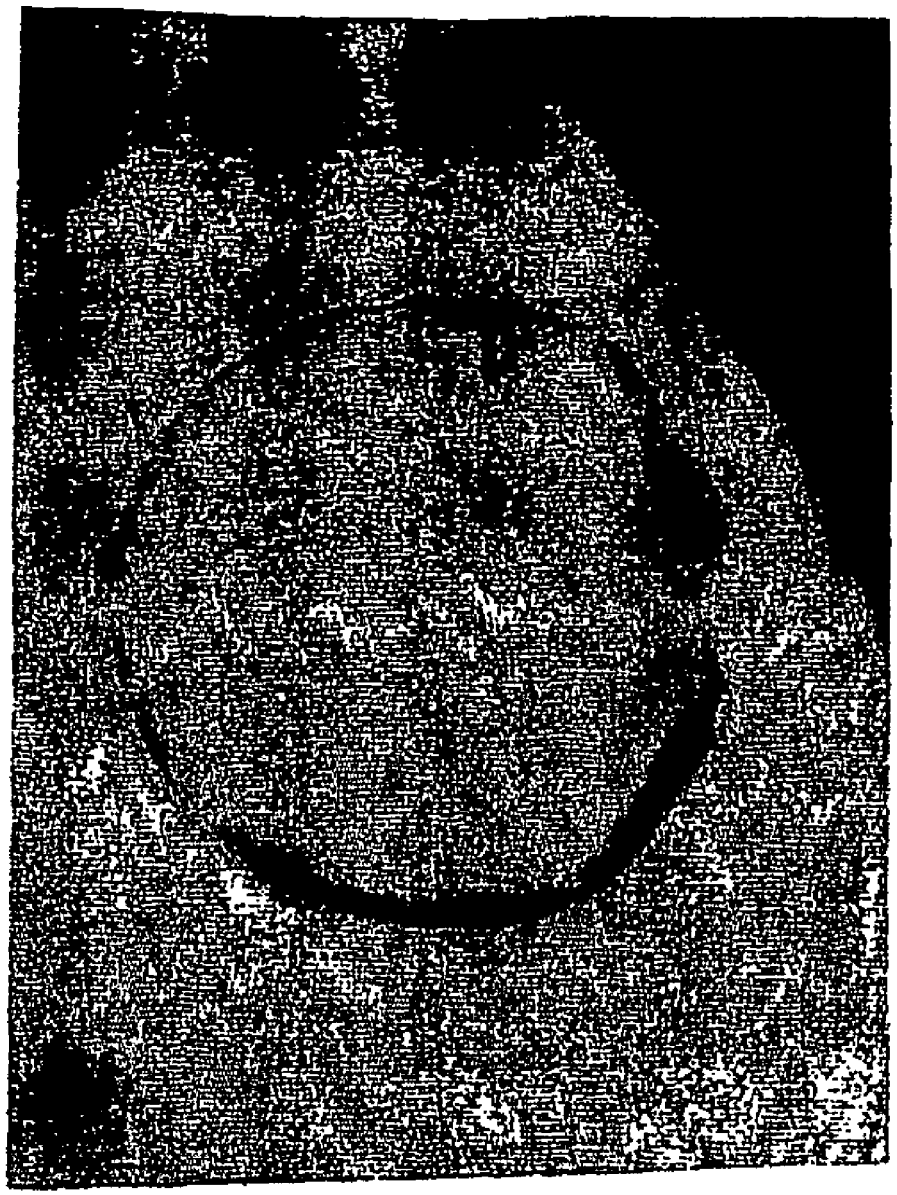
FIG. 3 is a picture of an experimentally produced protein lattice of the type illustrated in FIG. 1.

This vector was transformed into *E. Coli* strain B834 (pLysS) for expression. Induction of expression was as follows: a 10 ml overnight culture of the expression strain (in LB broth containing 30 µg/ml Kanamycin) was diluted 1:100 into fresh LB broth containing 30 µg/ml Kanamycin. Cells were grown with shaking at 37° C. to a density corresponding to an $OD_{600}$ of 0.6 and were then induced to express the target protein by the addition of IPTG to a final concentration of 1 mM. The culture was maintained at 37° C. with shaking for a further 3 hours before the cells were harvested by centrifugation (5000 g, 10 min, 4° C.). The cell pellet was resuspended in 20 ml of buffer A (300 mM NaCl, 1 mM EDTA, 50 mM HEPES, pH7.5). Cells were lysed by sonication and the insoluble fraction harvested by centrifugation (25,000 g, 30 min, 4° C.) to remove insoluble particles. The urea solubilised material was concentrated to 16 mg/ml and passed through a 0.22 µm filter. A drop of this material (1 µl) was then directly injected into a larger drop (5 µl) of buffer A. Protein lattice particles were observed within one hour. FIG. 3 is a picture of one of the protein lattice particles having a diameter of approximately 0.6 mm. The elemental composition of the protein lattice has been confirmed using µPIXE techniques.

Protein lattices in accordance with the present invention have numerous different uses. In general, such uses will take advantage of the regular repeating structure and the pores within the lattice. Lattices in accordance with the present invention may be designed to have pores with dimensions expected to be of the order of nanometers to hundreds of nanometers. Lattices may be designed with an appropriate pore size for a desired use.

The highly defined, unusually sized and finely controlled pore sizes of the protein lattices together with the stability of their lattice structures make them ideal for applications requiring microporous materials with pore sizes in the range just mentioned. As one example, the lattices are expected to be useful as a filter element or molecular sieve for filtration or separation processes. In this use, the pore sizes achievable and the ability to design a pore's size would be particularly advantageous.

In another class of use, macromolecular entities would be attached to the protein lattice. Such attachment may be done using conventional techniques. The macromolecular entities may be any entities of an appropriate size, for example proteins, polynucleotides or non-biological entities. As such, the protein lattices are expected to be useful as biological matrices for carrying macromolecular entities, for example for use in drug delivery, or for crystallizing macromolecular entities.

Attachment of the macromolecular entities to the protein lattice may be performed by "tagging" either or both of the protein protomers or the macromolecular entities of interest. In this context, tagging is the covalent addition to either or both of the protein protomers or the target macromolecular entities, of a structure known as a tag which forms strong interactions with a target structure. The target structure may be a further tag attached to the other of the protein protomer or target macromolecular entity, or may be a part of the protein protomer or target macromolecular entity. In the case of the protein protomer, or a macromolecular entities which is a protein, this may be achieved by the expression of a genetically modified version of the protein to carry an additional sequence of peptide elements which constitute the tag, for example at one of its termini, or in a loop region. Alternative methods of adding a tag include covalent modification of a protein after it has been expressed, through techniques such as intein technology.

Thus to attach the macromolecular entity to the protein lattice, the protein protomers may include, at a predetermined position in the protomers, an affinity tag attached to the macromolecular entity of interest.

Alternatively, the macromolecular entity of interest may have at a predetermined position in the protomers, an affinity tag attached to a macromolecular entity.

When a component of the protein lattice is known to form strong interactions with a known peptide sequence, that peptide sequence may be used as a tag to be added to the target macromolecular entity. Where no such tight binding partner is known, suitable tags may be identified by means of screening. The types of screening possible are phage-display techniques, or redundant chemical library approaches to produce a large number of different short (for example 3-50 amino acid) peptides. The tightest binding peptide elements may be identified using standard techniques, for example amplification and sequencing in the case of phage-displayed libraries or by means of peptide sequencing in the case of redundant libraries.

To attach the macromolecular entity to the protein lattice using an affinity tag on the lattice or the macromolecular entity, the macromolecular entity may be allowed to diffuse into, and hence become attached to, a pre-formed protein lattice, for example by annealing of the bound macromolecular entity into their lowest energy configurations in the protein lattice may be performed using controlled cooling in a liquid nitrogen cryostream. Alternatively, the macromolecular entities may be mixed with the protomers during formation of the protein lattice to assemble with the lattice.

In another class of uses, proteins having useful properties could be incorporated as one of the protomers.

A use in which an entity is attached to the protein lattice is to perform X-ray crystallography of the macromolecular entities. In this case, the regular structure of the protein lattice allows the macromolecular entities to be held in an array at a predetermined position relative to a repeating unit, so that they are held in a regular array and in a regular orientation. X-ray crystallography is important in biochemical research and rational drug design.

The protein lattice having an array of macromolecular entities supported thereof may be studied using standard x-ray crystallographic techniques. Use of the protein lattice as a support in x-ray crystallography is expected to provide numerous and significant advantages over current technology and protocol for X-ray crystallography, including the following:

(1) Significantly lower amounts of macromolecule will be required (probably of order micrograms rather than milligrams). This will allow determination of some previously intractable targets.
(2) Use of affinity tags will allow structure determination without the typical requirement for a number of purification steps.
(3) There will be no need to crystallize the macromolecular entity. This is a difficult and occasionally insurmountable step in traditional X-ray structure determination.
(4) There will be no need to obtain crystalline derivatives for each novel crystal structure to obtain the required phase information. Since the majority of scattering matter will be the known protein lattice in each case, determination of the structure may be automated and achieved rapidly by a computer user with little or no crystallographic expertise.
(5) The complexes of a protein with chemicals (substrates/drugs) and with other proteins can be examined without requiring entirely new crystallization conditions.
(6) The process is expected to be extremely rapid and universally applicable, which will provide enormous savings in time and costs.

For use in catalysing biotransformations, enzymes may be attached to the protein lattice, or incorporated in the protein lattice.

For use in data storage, it may be possible to attach a protein which is optically or electronically active. One example is Bacteriorhodopsin, but many other proteins can be used in this capacity. In this case, the protein lattice would hold the attached protein in a highly ordered array, thereby allowing the array to be addressed. The protein lattice is expected to be able to overcome the size limitations of existing matrices for holding proteins for use in data storage.

For use in a display, it may be possible to attach a protein which is photoactive or fluorescent. In this case, the protein lattice would hold the attached protein in a highly ordered array, thereby allowing the array to be addressed for displaying an image.

For use in charge separation, a protein which is capable of carrying out a charge separation process may be attached to the protein lattice, or incorporated in the protein lattice. Then the protein may be induced to carry out the separation, for example biochemically by a "fuel" such as ATP or optically in the case of a photoactive centre such as chlorophyll or a photoactive protein such as rhodopsin. A variety of charge separation processes might be performed in this way, for example ion pumping or development of a photo-voltaic charge.

For use as a nanowire, a protein which is capable of electrical conduction may be attached to the protein lattice, or incorporated in the protein lattice. Using an anisotropic protein lattice, it might be able to provide the capability of carrying current in a particular direction.

For use as a motor, proteins which are capable of induced expansion/contraction may be incorporated into the protein lattice.

The protein lattices may be used as a mould. For example, silicon could be diffused or otherwise impregnated into the pores of the protein lattice, thus either partially or completely filling the lattice interstices. The protein material comprising the original lattice may, if required, then be removed, for example, through the use of a hydrolysing solution.

The invention claimed is:

1. A protein lattice having a regular structure with a repeating unit repeating in three dimensions,
the repeating unit comprising protein protomers, wherein each protein protomer comprises at least a first monomer and a second monomer genetically fused together or chemically fused together by a covalent linkage, the monomers each being a monomer of an oligomer assembly into which the monomers are assembled for assembly of the protomers into the lattice, and
wherein said first monomer is a monomer of a first oligomer assembly which has at least three rotational symmetry axes; and
wherein said second monomer is a monomer of a second oligomer assembly, said second oligomer assembly having a rotational symmetry axis of the same order as one of the at least three rotational symmetry axes of the first oligomer assembly and being aligned with the one of the at least three rotational symmetry axes of the first oligomer assembly when said protomers self-assemble into the lattice.

2. The protein lattice according to claim 1, wherein the orders of the rotational symmetry axes of said at least three rotational symmetry axes are independently selected from the group consisting of 2, 3, 4 and 6.

3. The protein lattice according to claim 1, wherein, in said protomers, said monomers are genetically fused via a linking group.

4. The protein lattice according to claim 3, wherein the linking group fuses the first and second monomers in the protomer at each monomer's terminus to reduce deformation of the monomers and facilitate said alignment of the rotational symmetry axes.

5. The protein lattice according to claim 1, wherein the protomers are homologous, all protomers in the protein lattice having the same set of monomers.

6. The protein lattice according to claim 5, wherein said first oligomer assembly belongs to either a tetrahedral point group or an octahedral point group.

7. The protein lattice according to claim 6, wherein said second oligomer assembly belongs to a dihedral point group of the same order as the one of said set of rotational symmetry axes of said first oligomer assembly.

8. The protein lattice according to claim 6, wherein said second oligomer assembly belongs to either a tetrahedral point group or an octahedral point group.

9. The protein lattice according to claim 5, wherein said first oligomer assembly belongs to a dihedral point group of order 3, 4, or 6, and said protomers comprise at least two second monomers with a second monomer fused to each terminus of said first monomer of said first oligomer assembly.

10. The protein lattice according to claim 9, wherein one of said second monomers is a monomer of an oligomer assembly which belongs to a dihedral point group of the same order as the dihedral point group to which the first oligomer assembly belongs.

11. The protein lattice according to claim 10, wherein the other of said second monomers is a monomer of an oligomer assembly which belongs to a dihedral point group of order 2.

12. The protein lattice according to claim 1, wherein the protomers are heterologous, comprising at least two different types of protomers in the protein lattice.

13. The protein lattice according to claim 12, wherein the repeating unit comprises protomers of two types, a first type of protomer and a second type of protomer, and wherein each of the two types of protomers has: (1) one monomer selected from a homologous oligomer assembly consisting of the same type of monomers; and (2) one monomer selected from a heterologous oligomer assembly consisting of two different types of monomers.

14. The protein lattice according to claim 13, wherein said first type of protomer in the repeating unit has a first monomer being assembled into said first oligomer assembly that is homologous and said first monomer of the first type of protomer fused to a second monomer which is one of said two different types of monomers of the heterologous oligomer assembly, and wherein said second type of protomer has a first monomer being assembled into a third oligomer assembly that is homologous and said first monomer of the second type of promoter is fused to a second monomer in the second type of protomer, said second monomer in the second type of protomer being the other of the two different types of monomers of said heterologous oligomer assembly.

15. The protein lattice according to claim 14, wherein said first oligomer assembly into which the first type of protomer assembles belongs to either a tetrahedral point group or an octahedral point group.

16. The protein lattice according to claim 14, wherein said third oligomer assembly belongs to a dihedral, tetrahedral or octahedral point group of the same order as said heterologous oligomer assembly.

17. The protein lattice according to claim 14, wherein said heterologous oligomer assembly belongs to a cyclic point group, wherein one of the rotational symmetry axes of said heterologous oligomer assembly is aligned with the rotational symmetry axes of the first and third oligomer assemblies.

18. The protein lattice according to claim 1 having an array of macromolecular entities attached thereto.

19. The protein lattice according to claim 18, wherein the protomers have, at a predetermined position in the protomers, an affinity tag attached to a macromolecular entity.

20. The protein lattice according to claim 18, wherein the macromolecular entities have a peptide affinity tag attached to one of the protomers in the protein lattice.

21. A method of supporting macromolecular entities for x-ray crystallography comprising: 1) providing a protein lattice according to claim 1 as a support; 2) placing an array of macromolecular entities into a protein lattice according to claim 1; and 3) performing x-ray crystallography of the macromolecular entities.

22. A method of performing x-ray crystallography comprising supporting an array of macromolecular entities on a protein lattice according to claim 1 and performing x-ray crystallography on the lattice having the macromolecular entities supported thereon.

23. A polynucleotide encoding a protein protomer according to claim 1.

24. A vector capable of expressing a protomer according to claim 1.

25. A host cell comprising a vector according to claim 24.

26. A method of making a protein protomer according to claim 1, comprising expressing a polynucleotide sequence which encodes the protomer in a host cell and, optionally, purifying the expressed protomer.

27. The protein lattice according to claim 5, wherein said first oligomer assembly and said second oligomer assembly have a rotational symmetry axis of order four (4) and are independently selected from the group consisting of human ferritin heavy chain, *Escherichia coli* (*E. coli*) dihydrolipoamide succinyltransferase, *Azotobacter vinelandii* dihydrolipoamide acetyltransferase, *E. coli* PurE and Sipunculid worm hemerythrin.

28. The protein lattice according to claim 27, wherein said first oligomer assembly is *Escherichia coli* PurE and said second oligomer assembly is human ferritin heavy chain.

29. The protein lattice according to claim 5, wherein said first oligomer assembly and said second oligomer assembly have a rotational symmetry axis of order three (3) and are independently selected from the group consisting of human 6-pyruvoyl tetrahydropterin synthase (PTPS), rat 6-pyruvoyl tetrahydropterin synthase (PTPS), *Escherichia coli* dps, *Staphylococcus epidermis* EpiD and *Escherichia coli* amino acid aminotransferase.

30. The protein lattice according to claim 29, wherein said first oligomer assembly is *Escherichia coli* dps and said second oligomer assembly is human PTPS.

31. The protein lattice according to claim 5, wherein said first oligomer assembly and said second oligomer assembly have a rotational symmetry axis of order two (2) and are independently selected from the group consisting of human Mn superoxide dismutase and *Plasmodium falciparum* lactate dehydrogenase.

32. The protein lattice according to claim 17, wherein said first homologous oligomer assembly and said third homologous oligomer assembly have a rotational symmetry axis of order four (4) and independently selected from the group consisting of human ferritin heavy chain, *Escherichia coli* (*E. coli*) dihydrolipoamide succinyltransferase, *Azotobacter vinelandii* dihydrolipoamide acetyltransferase, *E. coli* PurE and Sipunculid worm hemerythrin; and wherein said heterologous assembly is Erachiopod hemerythrin.

33. The protein lattice according to claim 17, wherein said first homologous oligomer assembly and said third homologous oligomer assembly have a rotational symmetry axis of order two (2) and are independently selected from the group consisting of human Mn superoxide dismutase and lactate dehydrogenase; and wherein said heterologous assembly contains human casein kinase alpha and beta chains.

34. The protein lattice according to claim 17, wherein said heterologous assembly has a rotational symmetry axis of order three (3) and is selected from the group consisting of:
  i. Coliphate T4 gp5 gp27;
  ii. human immunovirus N36 C34; and
  iii. *Pseudomonas putida* napthalene 1,2-dioxygenase, and wherein said first oligomer assembly and said third homologous oligomer assembly have a rotational symmetry axis of order three (3) and are independently selected from the group consisting of:
  i. human 6-pyruvoyl tetrahydropterin synthase (PTPS);
  ii. rat 6-pyruvoyl tetrahydropterin synthase;
  iii. *Escherichia coli* dps;
  iv. *Staphylococcus epidermis* EpiD; and
  v. *Escherichia coli* amino acid aminotransferase.

* * * * *